(12) United States Patent
Cherukuri

(10) Patent No.: US 7,229,641 B2
(45) Date of Patent: *Jun. 12, 2007

(54) RAPID-MELT COMPOSITIONS METHODS OF MAKING SAME AND METHODS OF USING SAME

(75) Inventor: S. Rao Cherukuri, Frederick, MD (US)

(73) Assignee: Capricorn Pharma, Inc., Frederick, MD (US)

( * ) Notice: Subject to any disclaimer, the term of this patent is extended or adjusted under 35 U.S.C. 154(b) by 497 days.

This patent is subject to a terminal disclaimer.

(21) Appl. No.: 10/208,877

(22) Filed: Aug. 1, 2002

(65) Prior Publication Data

US 2002/0187188 A1    Dec. 12, 2002

Related U.S. Application Data

(63) Continuation-in-part of application No. 09/858,885, filed on May 17, 2001, now Pat. No. 6,589,556, which is a continuation-in-part of application No. 09/610,489, filed on Jul. 5, 2000, now Pat. No. 6,375,982.

(51) Int. Cl.
*A61K 9/20* (2006.01)
*A61K 9/14* (2006.01)

(52) U.S. Cl. ........................ 424/465; 424/484
(58) Field of Classification Search ............ 424/484, 424/488, 464, 497, 465
See application file for complete search history.

(56) References Cited

U.S. PATENT DOCUMENTS

| | | | |
|---|---|---|---|
| 4,327,076 A * | 4/1982 | Puglia et al. | ............... 424/441 |
| 4,327,077 A | 4/1982 | Puglia et al. | |
| 4,446,135 A | 5/1984 | Fountaine | |
| 4,609,543 A | 9/1986 | Morris et al. | |
| 4,684,534 A | 8/1987 | Valentine | |
| 4,937,076 A | 6/1990 | Lapidus | |
| 5,320,848 A | 6/1994 | Geyer et al. | |
| 5,753,255 A * | 5/1998 | Chavkin et al. | ............ 424/441 |
| 5,837,285 A | 11/1998 | Nakamichi et al. | |
| 5,840,334 A * | 11/1998 | Raiden et al. | ............... 424/464 |
| 5,989,583 A | 11/1999 | Amselem | |
| 6,024,981 A | 2/2000 | Khankari et al. | |
| 6,248,363 B1 * | 6/2001 | Patel et al. | .................. 424/497 |
| 6,375,982 B1 * | 4/2002 | Cherukuri | .................... 424/484 |
| 6,589,556 B2 * | 7/2003 | Cherukuri | .................... 424/484 |

FOREIGN PATENT DOCUMENTS

| | | |
|---|---|---|
| GB | 2 195 891 | 4/1988 |
| GB | 2 195 892 | 4/1988 |

* cited by examiner

*Primary Examiner*—Michael G. Hartley
*Assistant Examiner*—Blessing Fubara
(74) *Attorney, Agent, or Firm*—Thorpe North & Western LLP

(57) ABSTRACT

A novel rapid-melt composition, including methods of making the same, and methods of using the same for the delivery of prophylactic and therapeutic active materials to a mammal. The rapid-melt compositions are formed by molding or compression, with an additional heating step being preferred.

7 Claims, No Drawings

RAPID-MELT COMPOSITIONS METHODS OF MAKING SAME AND METHODS OF USING SAME

This application is Continuation-In-Part of patent application Ser. No. 09/853,885 filed May 17, 2001 now U.S. Pat. No. 6,589,556 which is a Continuation-In-Part of patent application Ser. No. 09/610,489 filed Jul. 5, 2000 and is now U.S. Pat. No. 6,375,982, the entire contents of which are hereby incorporated by reference in their entirety.

BACKGROUND OF THE INVENTION

1. Field of the Invention

The present invention relates to a rapid-melt composition for delivery of prophylactic and therapeutic active materials to a mammal, methods of making the same, and methods of using the same. Preferably, the prophylactic or therapeutic active is a psychotropic, a gastrointestinal therapeutic or a migraine therapeutic.

2. Description of the Prior Art

Pharmaceutical compositions may be produced in a variety of dosage forms, depending upon the desired route of administration of the therapeutic material. Oral dosage forms, for example, include such solid compositions as tablets, emulsions, and suspensions. The particular dosage form utilized will depend on such factors as the solubility and chemical reactivity of the pharmaceutical active. Further, the dosage form may be selected so as to optimize delivery of the pharmaceutical active and/or consumer acceptability of the composition.

Tablet compositions offer many advantages, including ease of product handling, chemical and physical stability, portability (in particular, allowing ready availability to the consumer when needed), aesthetic acceptability and dosage precision, i.e., ensuring consistent and accurate dosages of the pharmaceutical active. However, liquid formulations may offer advantages in the treatment of certain disorders, such as disorders of the upper gastrointestinal tract, wherein delivery of an active material dissolved or dispersed in a liquid ensures rapid and complete delivery to the afflicted area. In an effort to obtain the therapeutic advantages associated with liquid formulations as well as the broad advantages associated with solids, many chewable tablet formulations have been developed.

One important factor in formulating chewable tablets is palatability and mouth feel, especially in tablets that include pharmaceutical dosages. Many pharmaceutical and confectionery tablets are designed to be chewed either to provide proper flavor or to increase the surface area of a particular drug to permit rapid activity in the digestive tract or circulatory systems. However, many pharmaceutical ingredients usually have both an unpleasant mouth feel and unpalatable taste due to chalkiness, grittiness, dryness and astringent properties of these materials. Accordingly, the practical value of these materials is substantially diminished since patients finding them objectionable may fail to take them as prescribed. A number of formulations have been investigated to ease the mouth feel and palatability of such compositions.

Khankari et al., U.S. Pat. No. 6,024,981, discloses a rapidly dissolving robust dosage form directed to a hard tablet that can be packaged, stored and processed in bulk. The solid tablet dissolves in the mouth of a patient with a minimum of grit. The tablet contains an active ingredient mixed into a matrix of a non-direct compression filler and a relatively high lubricant content.

Amselem, U.S. Pat. No. 5,989,583, discloses a dry solid lipid composition suitable as an oral dosage form. The composition contains a lipophilic substance, at least one fat which is a solid at about 25° C. and at least one phospholipid present in an amount of about 2 to 40% by weight of the composition. However, the resultant product is a dry solid lipid composition.

United Kingdom patent application GB 2 195 892 discloses pharmaceutical chewable tablets with improved palatability. The lipid-containing molded tablets include a lipid material having a melting point from about 26° C. to about 37° C., a particulate dispersant material, an emulsifier and a safe and effective amount of a pharmaceutically active material. The tablets of the lipid composition exhibit improved palatability, and effective dispersion in the mouth and stomach.

United Kingdom patent application GB 2 195 891 also discloses pharmaceutical chewable tablets with improved palatability. The lipid-containing molded tablets include a lipid material, a dispersant, a nonionic emulsifier having an HLB of at least 10, and a safe and effective amount of a pharmaceutical active material, wherein the average HLB of all emulsifiers in the composition is at least about 8.

Nakamichi et al., U.S. Pat. No. 5,837,285, discloses fast soluble tablets that can be produced by a simple method. The tablet base is a sugar alcohol. The mixture of the sugar alcohol and a drug is subjected to compressive shaping prior to drying in the process. The dry solid tablet can be produced by modification of conventional tableting technology and possesses physico-chemical stability.

Chavkin et al., U.S. Pat. No. 5,753,255 discloses a chewable medicinal tablet. The tablet contains about 30 to about 95% by weight of a capric triglyceride and a medicinally active ingredient up to 60% by weight. If the medicinally active ingredient is less than about 30% by weight, then the composition also contains up to 10% by weight of a member of the group consisting of glyceryl monostearate, a mixture of glyceryl monostearate and glyceryl monopalmitate, and a mixture of glyceryl monostearate and glyceryl distearate.

Geyer et al., U.S. Pat. No. 5,320,848, discloses a non-aqueous chewable composition for oral delivery of unpalatable drugs. The drug is intimately dispersed or dissolved in a pharmaceutically-acceptable lipid that is solid at room temperatures. The lipid material desirably readily melts with the application of mild temperatures, i.e. about 55 to 95° C.

Lapidus, U.S. Pat. No. 4,937,076, discloses a chewable aspirin and buffering material tablet in a single dosage form. The buffering materials are integrally dispersed and bound in a fatty material of chocolate, synthetic chocolate or hydrogenated tallow. The fatty material individually coats the aspirin and buffering material.

Valentine, U.S. Pat. No. 4,684,534, discloses quick-liquefying, chewable tablets. The tablets have a harder outer shell which inhibits penetration of liquid, and a softer interior which quickly liquefies when the tablet and shell are broken into pieces and contacted by the liquid. The excipient or base material of the tablet is made from carbohydrates held together with small quantities of a carbohydrate binder such as maltodextrin. The tablets can contain active ingredients such as pharmaceuticals, breath sweeteners, vitamins and dietary supplements.

Morris et al., U.S. Pat. No. 4,609,543, discloses a soft homogeneous antacid tablet. The tablet contains solid antacid particles thoroughly coated with a mixture composed of a fatty material or oil, a surfactant, and a flavor. The fat or oil is present in an amount of from about 25% to about 45% of the mixture. The primary particle size of the antacid is less than 100 millimicrons.

Fountaine, U.S. Pat. No. 4,446,135, discloses chewable calcium carbonate-containing antacid tablets having good mouth feel properties. The good mouth feel properties of the tablet are obtained by using calcium carbonate of a particular particle size in combination with certain excipients. The calcium carbonate is present in an effective amount and has a size from about 5 to 50 microns in diameter.

Puglia et al., U.S. Pat. No. 4,327,077, discloses a compressed chewable antacid tablet which has good flexibility, is breakage resistant and disintegrates immediately upon chewing. The tablet is formed of a recrystallized fatty material, such as chocolate, a bulking material and an active ingredient bound up in the particles of the recrystallized fatty material. The preferred recrystallized fatty material is a chocolate or a synthetic chocolate.

Puglia et al., U.S. Pat. No. 4,327,076, also discloses a compressed chewable antacid tablet which has good flexibility, is breakage resistant and disintegrates immediately upon chewing. The tablet is formed of particles of the antacid or other active ingredient which are admixed with particles formed of edible fat or oil absorbed on a fat-absorbing material, such as microcrystalline cellulose. Upon chewing, the tablet is quickly converted to a smooth creamy non-gritty palatable emulsion.

However, the prior art compositions contain various disadvantages. For example, tablets may be incompletely chewed due to the poor palatability of the composition. Such compositions may also have a gummy texture, and are subject to "taste fatigue," i.e., the composition is perceived to be less palatable after ingestion of multiple doses. Further, the binders and other materials used in such chewable tablets may prevent rapid and effective delivery of active materials to the stomach.

There is a need for a rapid-melt, composition that behaves like a liquid when consumed by a mammal, and yet acts like a solid in many other ways. The need extends for compositions in which no biting or chewing is necessary in order for the composition to melt in the mouth of a mammal. Such compositions are ideal for uses in the fields of pediatric and geriatric care, that is, for use with people or mammals that do not have any teeth.

It has been found that product formulations containing one or more certain lipid materials, emulsifiers and particulate materials are highly palatable and effective compositions for the delivery of pharmaceutical active materials. Such compositions afford better taste, mouth feel and storage stability than those compositions known in the art.

BRIEF SUMMARY OF THE INVENTION

Applicant has unexpectedly developed a method of preparing a rapid-melt composition comprising the steps of:
a) melting at least one binder in an amount from about 0.01% to about 70% by weight with a salivating agent in an amount from about 0.05% to about 15% by weight, to form a first mixture;
b) mixing a therapeutically effective amount of an active ingredient with at least one lubricant to form a second mixture;
c) combining said first mixture with said second mixture to form a compressible mixture; and
d) compressing said compressible mixture into said rapid-melt composition.

Applicant has further developed a method of preparing a rapid-melt composition comprising the steps of:
a) melting at least one binder in an amount from about 0.01% to about 70% by weight with a salivating agent in an amount from about 0.05% to about 15% by weight, to form a first mixture;
b) mixing a therapeutically effective amount of an active ingredient with at least one lubricant to form a second mixture;
c) combining said first mixture with said second mixture to form a compressible mixture;
d) compressing said compressible mixture into said rapid-melt composition;
e) heating said rapid-melt composition to a temperature 40 to 60° C. for a period of 1 to 10 minutes in order to convert said binder to a bonding agent; and
f) cooling said heated rapid-melt composition.

Further, Applicant has unexpected developed a method for preparing a compressed rapid-melt composition comprising the steps of:
a) mixing at least one diluent present in an amount of 0.1 to 70% by weight with a therapeutically effective amount of an active ingredient and a binding agent in an amount which is less than required to fully bind said diluent and said active ingredient;
b) granulating said mixture from step a) to form granules;
c) mixing said granules with a bonding agent in an amount of 5 to 30% by weight to form a compressible mixture; and
d) compressing said compressible mixture into said rapid-melt composition.

The rapid-melt, semi-solid molded compositions of the present inventive subject matter exhibit good resistence to prolonged exposure to heat and the atmosphere. More particularly, the compositions surprisingly maintain their texture and rapid melting properties when exposed to those elements.

DETAILED DESCRIPTION OF THE EMBODIMENTS

The rapid-melt compositions of the present inventive subject matter contains at least one binder, a salivating agent, an active material, and a diluent/bulking material. The rapid-melt compositions may also contain a slipping agent to aid in the transport of the composition from the mouth of the mammal to the stomach thereof.

As used herein, the expression "mammal" includes without limitation any mammalian subject, such as mice, rats, guinea pigs, cats, dogs, human beings, cows, horses, sheep or other livestock.

As used herein, the expression "free water" means water that is not found in other ingredients. Many ingredients used in the present inventive compositions may also have water as part of the ingredient, and the term "free water" refers to water that is separate from those ingredients.

The unique novel combination of elements allows for fast melting of the composition when placed in the mouth of a user. By pressing the composition between the tongue and cheek of the user, the saliva of the user provides hydration to the composition and allows the composition to melt without any chewing. A unique feature of the present inventive compositions is that the composition becomes a liquid upon the application of pressure. The compositions rapidly melt upon the application of pressure by the tongue of the patient, thus forming a liquid carrier for the active ingredients contained therein. The liquid helps provide the unique characteristics and features of the present inventive compositions.

The liquification of the inventive compositions can be achieved through the application of pressure by the tongue of the patient, as described above. Optionally, the liquification may be attained by the patient chewing the compositions. A slight amount of chewing will enhance the liquefication of the compositions. A further way for the composition to be liquified is by the patient sucking on the rapid-melt, compositions of the inventive subject matter.

The rapid-melt technology of the present inventive subject matter has multiple applications which are ideal for the unique properties of the compositions. One such application is the delivery of active ingredients to a mammal in need thereof.

In addition, the melting feature of the novel compositions makes the compositions ideal for uses in pediatric and geriatric care, since small children and aged individuals often have difficulty chewing items. With this intended use in mind, the compositions may be specially formulated for pediatric and geriatric patients. The unique properties will aid in drug compliance by such patients as the drugs may be administered in a way that will not require chewing by the patient.

Another application for which the inventive compositions are ideal is to enhance the saliva flow of a patient. A frequent problem for geriatric patients is dry-mouth, or the inability to salivate sufficiently. The aid of saliva flow by the use of the present inventive compositions will enhance tooth cleaning within the patient, as well as stimulate better drug delivery to the patient. Also, the increased saliva flow will facilitate better breath characteristics in the patient. The use of xylitol, as well as other polyols and sugars, in the inventive compositions will contribute to the enhancement of the saliva flow of the patient.

A further application for the inventive compositions would be the preparation of compositions for drug delivery in diabetic patients. A diabetic patient must monitor the intake of sugar and the ability to formulate the present inventive compositions with fractose and other non-cariogenic components makes them ideal for delivery of drugs to diabetic patients.

The rapid-melt compositions of the present inventive subject matter are preferably anhydrous, that is, they do not contain any water. The lack of water in the inventive compositions allows high doses of active materials or combinations of active materials to be incorporated into the compositions due to the stability of the active materials in the absence of the water. It is contemplated, however, that the compositions may optionally include an amount of water. The amount of water present will depend on the active ingredients to be delivered, but generally will be present in an amount less than 2.0% by weight of the composition. Preferably, the water will be present in an amount less than 1.0% by weight of the composition.

The rapid-melt compositions of the present inventive subject matter contain at least one binder. As used herein, "binder" means at least one ingredient useful in keeping the composition in its state, may be either solid or liquid, and may include, without limitation, a high melting point fat or waxy material such as lipid materials, polyethylene glycols (PEG), waxes and other fats. Preferably, the semi-solid compositions of the present inventive subject matter contains a mixture of binders. The solid binders useful in the compositions of the present inventive subject matter have a melting point of about 25 to 90° C., and preferably about 37° C. When more than one binder is used in the inventive compositions, the melting point of the combination of the binders will remain within the range of 25 to 90° C., and preferably about 37° C. The inventive subject matter contemplates the use of mixtures of solid binders and liquid binders. For a non-limiting example, the present inventive subject matter contemplates mixing a small amount of a high-melting point lipid with a liquid binder to achieve a binder that attains the desired product characteristics. These characteristics include such factors as mouth feel, rapidity of melting in the mouth, appearance, flavor and compatibility with active materials and therapeutic active materials.

Among the lipid materials useful as binders in the compositions of the present inventive subject matter are those which are commercially available and commonly used in confectionery and other food products. Such lipid materials include, without limitation, cocoa butter, hydrogenated tallow, hydrogenated vegetable oils, hydrogenated cotton seed oil, palm kernel oil, soybean oil, stannol esters, and derivatives and mixtures thereof. Hydrogenated vegetable oils (such as hydrogenated palm kernel oil), cocoa butter, and cocoa butter substitutes are among the preferred useful lipid materials.

Other materials are also suitable as binders in the present inventive subject matter. Included within the materials suitable as binders are, without limitation, polyethylene glycols and liquid binders. Examples of liquid binders are, without limitation, poly saccharides, gum solutions, water, corn syrup, hydrogenated starch hydrolates, glycerine, polypropylene glycol, and mixtures thereof.

The amount of binder present in the rapid-melt composition of the present inventive subject matter is from about 0.01% to about 70% by weight of the final composition. Preferably, the amount of binder is from about 0.01% to about 50% by weight of the composition. More preferably the binder is present from about 15% to about 30% by weight of the composition.

The binder is used to provide good melt away properties to the composition while preventing a gritty texture being imparted by the composition. The binder aids in the fast melting of the composition when placed in the mouth of a user.

The rapid-melt composition of the present inventive subject matter also contains a salivating agent. As is used herein, "salivating agent" means a material that promotes greater salivation in the user of the compositions of the present inventive subject matter. The salivating agent helps create salivation in the mouth of the mammal using the inventive compositions. This is an important feature since the present compositions are intended to be taken by the patient without the aid of water to help in the transporting of the composition to the stomach of the patient. The salivating agent can be, without limitation, an emulsifier or a food acid that initiates salivation in the mouth of the patient.

Examples of emulsifiers useful as salivating agents in the compositions of the present inventive subject matter include, without limitation, alkyl aryl sulfonates, alkyl sulfates, sulfonated amides and amines, sulfated and sulfonated esters and ethers, alkyl sulfonates, polyethoxlyated esters, mono- and diglycerides, diacetyl tartaric esters of monoglycerides, polyglycerol esters, sorbitan esters and ethoxylates, lactylated esters, phospholipids such as lecithin, polyoxyethylene sorbitan esters, proplyene glycol esters, sucrose esters, and mixtures thereof. The emulsifier may be either saturated or unsaturated.

Examples of food acids useful as salivating agents in the inventive compositions include, without limitation, citric acid, malic acid, tartarate, food salts such as sodium chloride and salt substitutes, potassium chloride, and mixtures thereof.

The amount of salivating agent present in the rapid-melt, semi-solid molded composition of the present inventive subject matter is from about 0.05% to about 15% by weight of the final composition. Preferably, the amount of salivating agent from about 0.3% to 0.4% by weight of the composition.

Keeping the amount of salivating agent present in the inventive composition within these limits for weight percentage is important to enhance the desirable properties of the compositions. More particularly, the low amount of salivating agent present in the compositions aid in the compositions retaining the physical state and the rapidity of melting in the mouth of a mammal.

The rapid-melt compositions of the present inventive subject matter further contain a diluent/bulking material. The use of a diluent/bulking material is necessary to serve as a free-flow imparting agent which aids in the moisturizing of the composition when chewed, that is, the diluent/bulking material aids in the processability of the compositions. The diluent/bulking material also serves to reduce the concentration of the active materials and add bulk to the composition. Examples of diluent/bulking materials useful in the compositions of the present inventive subject matter include, without limitation, silicon dioxide, sugars, starches, lactose, sucrose, sorbitol, fructose, talc, stearic acid, magnesium stearate, dicalcium phosphate, erythitol, xylitol, mannitol, maltitol, isomalt, dextrose, maltose, lactose, microcrystalline celluloses and mixtures thereof.

The amount of diluent/bulking material present in the rapid-melt compositions is from about 10% to about 90% by weight of the final composition. Preferably, the amount of diluent/bulking material is from about 35% to about 55% by weight of the final composition.

The rapid-melt compositions of the present inventive subject matter may optionally contain a further slipping agent to aid in the palatability of the composition after it melts in the mouth of the mammal. The slipping agent may be a further lipid material, as is described above for binders, or another material which aids in the "slipping" of the composition through the mouth and down the esophagus of the mammal.

As is discussed above, the preferably anhydrous nature of the present inventive compositions allows for very high doses of active materials to be incorporated therein. The amount of active material present in the inventive compositions will vary depending on the particular active used, but generally will be present in an amount of about 0.001% to 70% by weight of the composition. Preferably, the active ingredients used in the inventive compositions are prophylactic or therapeutic active ingredients. Prophylactic or therapeutic active materials which can be used in the present invention are varied. A non-limiting list of such materials includes the following: antitussives, antihistamines, decongestants, alkaloids, mineral supplements, laxatives, vitamins, antacids, ion exchange resins, anti-cholesterolemics, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidrrheal preparations, anti-anginal drugs, vasodilators, anti-hypertensive drugs, vasoconstrictors, migraine treatments, antibiotics, tranquilizers, anti-psychotics, antitumor drugs, anticoagulants, antithrombotic drugs, hypontics, anti-emetics, anti-nausants, anti-convulsants, neuromuscular drugs, hyper- and hypoglycemic spasmodics, uterine relaxants, mineral and nutritional additives, antiobesity drugs, anabolic drugs, erythropoetic drugs, antiashmatics, cough suppressants, mucolytics, anti-uricemic drugs and mixtures thereof.

Preferred prophylactic or therapeutic active materials contemplated for use in the present inventive subject matter are analgesics. Examples of analgesics useful in the present inventive subject matter, and which are the preferred therapeutic active ingredients, include, without limitation, aspirin, acetaminophen, ibuprophen and mixtures thereof.

Another preferred active material can be selected from the class of prophylactic, abortive or analgesic drugs used to treat migraines. Migraines are defined as headaches that last 4 to 72 hours wherein the patient experiences moderate to severe cranial throbbing. Migraines are also associated with nausea, vomiting, or sensitivity to light, sound or smell.

For prophylactic treatment of migraines, β-blockers, calcium channel blockers, tricyclic antidepressants, or anticonvulsants can be used. Examples of drugs indicated for prophylactic treatment include amitriptyline, methysergide, popranolol, valproate, and verapamil.

For abortive treatment of migraines serotonin receptor activators such as eletriptan, ergotamine, naratriptan, rizatriptan benzoate, sumatriptan succinate, and zolmitriptan can be used. Ergot alkaloid derivatives such as ergoamine tartrate and dihydroergotamine are also effective. Dopamine antagonist anti-emetics such as metoclopramide and prochlorperazine while indicated for the treatment of nausea, can also be used even if nauseau is not prominent.

For analgesic treatment acetaminophen, aspirin, non-asteroidal anti-inflammatory drugs ("NSAID") and opioids can be used in the present invention.

Yet another preferred active material used in the composition of the present inventive matter is a psychotropic. Psychotropics are used to treat depression, schizophrenia, anxiety disorders, attention deficit order, obsessive compulsive disorder, senile dementia and certain sleep disorders.

The classes of drugs used in treating depression include selective serotonin reuptake inhibitors ("SSRI's"), heterocyclic antidepressants, monoamine oxidase inhibitors ("MAOI's"), serotonergic-noradrenergics, 5-HT$_2$ antagonists and catecholaminergics. Examples of SSRI'S include fluoxetine HCl, sertraline HCl, paroxetine HCl, and fluvoxamine. Examples of heterocyclic antidepressants include amitriptyline, nortriptyline, imipramine, desipramine, doxepin, trimipramine, clomipramine, protriptyline, amoxapine, and maprotiline. Examples of MAOI's include phenelzine and tranylcypromine. An example of a serotonergic-noradrenergics includes venlafaxine HCl. Examples of 5-HT$_2$ antagonists include trazadone, nefazodone, and mirtazapine. An example of a catecholaminergics includes bupropion. All examples are non-limiting and it will be understood that psychotropics of the disclosed classes may be used with the present inventive subject matter.

For the treatment of anxiety, benzodiazepines may be used with the present inventive subject matter. Specific examples include alprazolam, chlordiazepoxide, clonazepam, clorazepate, diazepam, lorazepam, and oxazepam. However, any class of psychotropic drug indicated for anxiety treatment may be used in the present invention.

For the treatment of insomnia, drugs belonging to the categories of benzodiazepines, imidazopyridines, antidepressants and non-prescription hypnotics may be used with the present inventive subject matter. Examples of benzodiazepines useful for the treatment of insomnia include midazolam, triazolam, oxazepam, temazepam, lorazepam, estazolam, nitrazepam, diazepam, quazepam, flurazepam, zopiclone and clorazepate. An example of an imidazopyridine includes zolpidem and zolpidem tartarate. Examples of antidepressants include amityiptyline and doxepin.

Still yet another preferred active material used in the composition of the present inventive matter is a gastrointestinal therapeutic. Gastrointestinal therapeutics are used to treat gastritis, nausea and vomiting, gastroesophegal reflux disease, colitis, Crohn's disease and diarrhea. Classes of drugs include proton pump inhibitors, histamine $H_2$ receptor antagonists, terpene analogs, and NSAID'S.

For the treatment of gastritis, drugs such as omeprazole, lansoprazole, ranitidine HCl, famotidine, nizatidine, teprenone, cimetidine, rabeprazole sodium, and sulpiride can be used in the compositions of the present inventive subject matter.

For the treatment of nausea and vomiting, drugs such as ondansetron HCl, granisetron HCl, dolasetron mesylate, and tropisetron may be used.

Another preferred active material used in the compositions of the present invention include cardiovascular therapeutics. Cardiovascular therapeutics treat hypertension, angina, myocardial infarction, congestive heart failure, acute coronary syndrome, edema, ventricular tachycardia, hyperaldosteronism, ventricular arrhythmia, cardiac insufficiency, atrial fibrillation, arterial occlusion, cardiac decompensation, and microcirculation activation.

A related class of cardiovascular therapeutics are cholesterol reducers such as 3-hydroxy-3-methylglutaryl coenzymeA ("HMG-CoA") reductase inhibitors. HMG-COA inhibitors work by blocking an enzyme used to make cholesterol. Blocking cholesterol thereby treats hypercholesterolemia which is a significant cause of cardiovascular disease.

For the treatment of hypercholesterolemia, drugs such as simvastin, atorvastatin calcium, pravastatin sodium, pravastatin, lovastatin, fluvastatin sodium, cerivastatin sodium can be used in the compositions of the present inventive subject matter.

For the treatment of hypertension, drugs such as amlodipine besylate, losartan potassium, lisinopril, felodipine, benazepril HCl, ramipril, irbesartan, verapamil HCl, bisoprolol fumarate and hydrochlorothiazide, amlodipine and benazepril HCl, clonidine, candesartan, cilexetil, diltiazem, nicardipine, imidapril, trandolapril, eprosartan mesylate, nilvadipine, verapamil HCl, temocapril, prazosin HCl, isradipine, cilazapril, celiprolol, bisoprolol, betazolol HCl, ramipril, nisoldipine, lisinopril, trandolapril, and nisoldipine can be used in the compositions of the present inventive subject matter.

For the treatment of congestive heart failure, drugs such as dioxin, carvedilol, spironolactone, trandolapril, and bisoprolol can be used in the compositions of the present inventive subject matter.

Still another preferred active material used in the composition of the present invention is a therapeutic useful for treating allergic rhinitis. The classes of compounds useful for treating allergic rhinitis include alkylamines, ethanolamines, ethylenediamines, piperazines, phenothiazine, piperdines, and nonsedating compounds.

Among the non-sedating compounds that can be used in the present invention are loratadine, fexofenadine HCl, certirizine HCl, and astemizole. Other drugs which can also be used are fluticasone propionate, mometasone furoate, epinastine, beclomethasone dipropionate, triamcinolone acetonide, budesonide, and azelastine.

Still yet another preferred active material used in the composition of the present invention is a therapeutic useful for treating osteoarthritis or rheumatoid arthritis. Rheumatoid arthritis is defined as non-specific, symmetrical inflammation of the peripheral joints, potentially resulting in progressive destruction of articular and periarticular structures. Osteoarthritis is characterized by loss of articular cartilage and hypertrophy of bone. Although osteoarthritis is a degenerative bone disease, symptoms associated with rheumatoid arthritis such as inflammation of the joints occur in a patient diagnosed with osteoarthritis. Accordingly, therapeutics treating rheumatoid arthritis can also be administered to an osteoarthritic patient.

Classes of drugs indicated for osteoarthritis and rheumatoid arthritis include cycloxygenase-2 inhibitors, NSAID'S, biologic response modifiers, pyrimidine synthesis inhibitors and hyaluronic acid. Specific examples of osteoarthritis and rheumatoid arthritis therapeutics include celecoxib, diclofenac sodium, rofecoxib, nabumetone, diclofenac sodium and misoprostol, oxaprozin, meloxicam, piroxicam, etodolac, naproxen, hylan G-F 20, leflunomide, tenoxicam, and naproxen sodium.

Another preferred active material used in the composition of the present invention is a therapeutic useful for treating benign prostatic hypertrophy. Benign prostatic hypertrophy is defined as an adenomatous hyperplasia of the periurethral part of the prostrate gland.

Classes of drug useful for the treatment of benign prostatic hypertrophy include alpha blockers, alpha-1 selective adrenoceptor blocking agents and 5-reductase inhibitors. Specific examples of benign prostatic hypertrophy therapeutics include doxazosin mesylate, terazosin HCl, tamsulosin, finasteride, tamsulosin HCl, ethinyl estradiol and levonorgestrel.

Yet another preferred active material used in the composition of the present invention is a drug indicated for the treatment of fungal infections. Classes of drugs indicated for the treatment of fungal infections include synthetic triazole, ergosterol inhibitor, and polyene antifungal. Specific examples of drugs indicated for the treatment of fungal infections are itraconazole, ketoconazole, and amphotericin B.

Still yet another preferred active material used in the composition of the present invention is a anti-convulsant. Anti-convulsants are drugs that prevent or relieve convulsions wherein the convulsions are due to epilepsy, seizure disorders, partial seizure disorders or Huntington's disease. Classes of drugs useful for treating these conditions include gamma-aminobutyric analogs, phenyltriazine, antiepileptic agents, benzodiazepines, polysynaptic response inhibitors, sulfamate-substituted monosaccharides, gamma-amino butyric acid uptake inhibitors and benzamides. Specific examples include carbamazepine, topiramate, and tigabine HCl.

Another preferred active material used in the composition of the present invention is an anti-herpetic. Anti-herpetics are used to treat infections from the varicella-zoster virus. Classes of drugs useful for treating herpes include synthetic purine nucleoside analogs, nucleoside analogs, and antiviral agents. Specific examples include acyclovir, valacyclovir HCL and famcyclovir.

Yet another active material used in the compositions of the present invention are anti-diarrheal therapeutics. Anti-diarrheal therapeutics treat the condition of diarrhea whether it is symptomatic of the disorder itself wherein diarrhea is a condition that occurs when a mammal has a low amount of stool in a bowel movement. Diarrhea results mainly from excess fecal water in the bowel of the mammal. Specific examples of anti-diarrheal therapeutics include loperamide HCl, diphenoxylate, codeine phosphate, camphorated opium tincture.

Further preferred nutritional active materials useful in the present inventive subject matter include, without limitation, calcium-containing materials such as calcium carbonate, vitamins, minerals, herbals, spices and mixtures thereof.

Examples of vitamins that are available as active ingredients include, without limitation, vitamin A (retinol), vitamin D (cholecalciferol), vitamin E group ($\alpha$-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final encapsulated product of the present inventive subject matter is dependent on the particular vitamin and is generally the United States' Department of Agriculture Recommended Daily Allowances (USRDA) for that vitamin. For example, if vitamin C is the active ingredient and the encapsulated product is being used in a confectionery or chewing gum targeting adults, the amount of vitamin C in the encapsulated product would be 60 milligrams, which is the USRDA of vitamin C for adults.

Examples of minerals that are available as active ingredients include, without limitation, calcium, magnesium, phosphorus, iron, zinc, iodine, selenium, potassium, copper, manganese, molybdenum and mixtures thereof. As is the case with vitamins, the amount of mineral or minerals present in the final encapsulated product of the present inventive subject matter is dependent on the particular mineral and is generally the USRDA for that mineral. For example, if iodine is the active ingredient and the encapsulated product is being used in a confectionery or chewing gum targeting adults, the amount of iodine in the encapsulated product would be 150 micrograms, which is the USRDA of iodine for adults.

Examples of herbals that are available as active ingredients include, without limitation, echinacea, peppermint, licorice, goldenseal, panax pseudoginseng, grapeseed extract, bilberry, kava, ginko biloba, panax quinquefolium, Siberian ginseng, St. John's wort, bromelian, guglupids, hawthorn, garlic, ginger, angelica species, dandelion, goldenseal, and mixtures thereof. Further, examples of spices that are available as active ingredients include, without limitation, mustard, dillweed, cinnamon, garlic, black pepper, onion, sage, oregano, basil, cream of tartar, targon, cayenne pepper, red pepper, and mixtures thereof. This list of herbals and spices is for exemplary purposes and is not meant to be construed as limiting the inventive subject matter thereto.

Many of the active material listed above have unpalatable tastes. Taste-masking of compositions with those unpalatable active materials is well-known in the art. The use of flavors and sweeteners to mask the unpalatability of the active materials is also well-known. Thus, other materials which can be incorporated into the rapid-melt composition of the present inventive subject matter include flavors, colors and sweeteners. A distinct feature of the inventive rapid-melt, compositions is that they exhibit excellent taste characteristics. Importantly, it is possible to incorporate high levels of flavors, sweeteners and other taste-masking agents, making the compositions more palatable when undesirable tastes accompany the active materials.

Flavors may be chosen from natural and synthetic flavor liquids. Flavors useful in the present inventive compositions include, without limitation, volatile oils, synthetic flavor oils, flavoring aromatics, oils, liquids, oleoresins or extracts derived from plants, leaves, flowers, fruits, stems and combinations thereof. A non-limiting list of examples include citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., betal-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), and mixtures thereof.

Further examples of flavors useful in the inventive compositions include, without limitation, beef flavorings, chicken flavorings, rice flavorings, lamb flavorings, pork flavorings, seafood flavorings, and mixtures thereof.

The sweeteners may be chosen from the following non-limiting list: flucose (corn syrup), dextrose, invert sugar, fructose, and mixtures thereof; saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, zylitol, and the like. Also contemplated are hydrogenated starch hydrolysates and synthetic sweetener 3,6-dihydro-6-methyl-1-1-1,2,3-oxathiazin-4- one-2,2-dioxide, particularly the potassium salt (acesulfame-K) and sodium and calcium salts thereof. Other sweeteners may also be used.

The rapid-melt compositions of the present inventive subject matter may also be coated in order to facilitate handling of the compositions. Coatings well-known in the art are useful for keeping the compositions from melting prior to being administered to a patient in need of an active material. By coating the compositions, the composition will maintain its state while being handled and will melt when inserted into a patient's mouth.

The present inventive subject matter also contemplates a method of preparing a rapid-melt composition. A preferred method involves the steps of: melting at least one binder having a melting point about 25 to 45° C. with a salivating agent to form a mixture; mixing an active material with the lipid material to form an active mixture; mixing a diluent/bulking material with said active material to form a final mixture; and molding the final mixture into the semi-solid molded composition. The method of the present inventive subject matter also contemplates adding other materials to the final mixture prior to molding into the semi-solid molded composition. Other materials which may be added to the final mixture prior to molding include, without limitation, flavors, colors, sweeteners, and mixtures thereof.

The amount of binder melted with the salivating agent is from about 10% to about 70% by weight of the final composition. Preferably, the amount of binder is from about 10% to about 50% by weight. More preferably the binder is present from about 15% to about 30% by weight. Likewise, the amount of salivating agent melted in the first step of the method is from about 0.2% to about 0.5% by weight of the final composition. Preferably, the amount of salivating agent is from about 0.3% to 0.4% by weight of the composition.

However, it should be recognized that the composition may be prepared by a variety of methods well-known by those of ordinary skill in the art. Such processes may be used on a batch or continuous process format and would involve melting the binders and uniformly blending them for suitable periods of time prior to adding the salivating agent. Once these two components have been blended together, the further components may be added either together or sequentially until a uniform mixture is obtained. It should also be recognized that the resulting mixture should be in a semi-solid state that may be poured into a mold, cast into preformed shapes, or stamped into the final products. Clearly, other tableting techniques are contemplated to be used herein.

In a preferred embodiment, the rapid-melt products of the present inventive subject matter are formed via compression of the ingredients. The compression of the ingredients into rapid-melt products may take place in a conventional compression or tableting machine such as a punch and die machine. In addition, the punches used in the punch and die machine may be modified with various materials to limit the formation of a film on the product when the same is punched into shape. One such modification would be to make the punch tips from a copper-beryllium alloy. The use of the copper-beryllium alloy on the tips of the punch, as well as blowing cold low-humidity air on the punch and dies before filling will aid in the reduction of film formation on the products.

Further, additional external lubrication could be added to the punch and die machine while forming the products. The external lubrication may be in the form of a powder lubricant applied via electrostatic method, or the external lubricant may be a liquid lubricant which is applied via conventional jet spraying techniques. In any of the above situations, the film formation during compression will be largely negated.

The binders present in the inventive rapid-melt formulations provide proper binding for the components of the formulation when formed by compression, thus no additional binders or other ingredients are needed. In other words, the binders already present in the inventive products provide enough binding characteristics that no additional binders are needed for the compression step. The fats and emulsifiers acting as the binding agents help form granules that impart flow and compression characteristics in the products.

In a particularly preferred embodiment, after the inventive rapid-melt product has been compressed, the compressed product is exposed to an elevated temperature. The conventional way to expose the compressed rapid-melt product is to employ a conveyor belt on which the compressed rapid-melt product is placed. The conveyor belt then passes through a heating zone, in which heat or hot air is applied to the compressed rapid-melt product. The interior of the compressed product is preferably not heated as much as the exterior of the compressed product. The heat or hot air heats the product or the surface of the product to a temperature of 40 to 60° C. for a period of 1 to 10 minutes. Preferably, the compressed rapid-melt product is heated to a temperature of 45 to 55° C. for a period of 2 to 5 minutes.

Conventional processes may be employed in order to heat the compressed rapid-melt products, with such conventional processes including, but not limited to, a conventional oven, a high voltage heat lamp, a microwave heating element, or the like. If a conventional conveyor belt is used in the heating step, preferably the conveyor will be a stainless steel screened type of conveyor. This will allow the heat to be applied to the product from both the top and the bottom.

In this preferred heating step, the compressed product is slightly heated, causing the emulsifier/fat system to soften or melt within the product. This melting results in the semi-liquid binding system changing its configuration in which the void spaces are filled by the softened or melted emulsifier/fat system present in the product. After the compressed product has been sufficiently heated, the product is cooled to room temperature. Even though the compressed product reaches room temperature relatively quickly, it takes the binding system several hours to return to its original form. This is due to the polymorphism of the emulsifier/fat system. During this time, the weak binding system (due to the relatively poor binding characteristics of the components) is converted to a bonding system between the particles in the compressed product. In this way, the fats and emulsifiers which may be considered weak binders when the compressed rapid-melt product is first granulated and compressed, the fats and emulsifiers now become a much stronger bonding system.

Optionally, the heating step of the inventive process may be done under vacuum, thus enhancing the bonding of the particles by the fat/emulsifier system.

One physical characteristic of the compressed rapid-melt product that is changed due to the bonding of the particles by the melted fat/emulsifier system is the friability of the compressed product. Due to the relatively weak binding characteristics of the fats and emulsifiers, the compressed rapid-melt product may be friable when first compressed. By surface heating the product and converting the binding system to a bonding system, the compressed product has a much higher integrity which allows it to be easily packaged. In other words, the tablet's friability has decreased significantly from very high to almost nothing. The tablet has a high integrity that is suitable for packaging in any form, including large bottles, and the stability of the compressed product is very good.

In a further preferred embodiment of the present inventive subject matter, the active ingredient is added to the compressed rapid-melt composition during the lubrication step of the process. That is, the active ingredient is added to the mixture at the same time that the lubricants are added to the mixture. By adding the active ingredient with the lubricants, the active ingredient is not exposed to the elevated temperatures used to melt the fats and emulsifiers. The lack of exposure to the higher temperature required to melt the fats and emulsifiers helps keep the integrity of the active ingredients intact, meaning that it is less likely for the active ingredients to decompose due to the elevated temperatures.

In addition to the fats and emulsifiers in the composition acting as lubricants (as well as binders), other lubricants may be added in order to enhance lubrication. Non-limiting examples of other lubricants include magnesium stearate, calcium stearate, talc, starches, silicon dioxide, and mixtures thereof.

As stated previously, it is an important aspect of the present inventive subject matter that the compressed rapid-melt product disintegrates quickly in the mouth of the mammal. Preferably, the compressed rapid-melt product disintegrates in less than 20 seconds of being placed in the mammal's mouth, preferably within 10 seconds, and more preferably within 7 seconds. In order to maintain this desired property, it is necessary to compress the components using a low compression force.

It is well-known in the art of compression that tablets are formed by using hard granules prepared by conventional processes, i.e., wet or dry granulation. In all of the conventional processes, strong binders are used to bind the granules and provide good compression and hard tablets when high compression forces are used. Thus, Applicant has found that using the low compressive forces to traditionally-prepared granules results in a compressed product that tend to be friable and fragile.

In a preferred embodiment of the present inventive subject matter, the granules may be prepared with less binding agent than is normally required. In general, the binding agent may be present only in enough amounts to convert the granular powders into the proper form for flowing within the compression machine. Applicant has determined that if granules prepared with less than the required amount of binding agent are then mixed with a bonding agent prior to compression with the low compressive pressures, the resultant product has much improved friability and is able to be handled and packaged more easily than those products prepared by the conventional method of tableting, while still maintaining the requisite disintegration time in the mouth of the user.

The bonding agent promotes good bonding between the particles of the compressed product, thus enhancing the integrity of the compressed product. The bonding agent does so by helping reduce the porosity, i.e. increase the density, in the compressed rapid-melt product and creating close bonds between the particles in the compressed rapid-melt products.

Typical bonding agents include, without limitation, polyethylene glycols in solid form (1450–3000 or more), monoglycerides (40–90% glycerides of vegetable or animal fats), acetylated monoglycerides, hydrocolloidal gums, other emulsifiers or fats and mixtures thereof. The amount of bonding agent present in the inventive subject matter is from 5 to 30% by weight. Preferably, the amount of bonding agent is 10 to 15% by weight.

Optionally, the compressed rapid-melt products prepared by this embodiment may be subjected to a heat treatment to further enhance the bonding as is discussed above. In particular, the compressed product is exposed to an elevated temperature. The conventional way to expose the compressed rapid-melt product is to employ a conveyor belt on which the compressed rapid-melt product is placed. The conveyor belt then passes through a heating zone, in which heat or hot air is applied to the compressed rapid-melt product. The heat or hot air heats the product to a temperature of 40 to 60° C. for a period of 1 to 10 minutes. Preferably, the compressed rapid-melt product is heated to a temperature of 45 to 55° C. for a period of 2 to 5 minutes.

Conventional processes may be employed in order to heat the compressed rapid-melt products, with such conventional processes including, but not limited to, a conventional oven, a high voltage heat lamp, a microwave heating element, or the like. If a conventional conveyor belt is used in the heating step, preferably the conveyor will be a stainless steel screened type of conveyor. This will allow the heat to be applied to the product from both the top and the bottom.

In this preferred heating step, the compressed product is slightly heated, causing the emulsifier/fat system to soften or melt within the product. This melting results in the semi-liquid binding system changing its configuration in which the void spaces are filled by the granules present in the product. The interior of the compressed product is preferably not heated as much as the exterior of the compressed product.

After the compressed product has been sufficiently heated, the product is cooled to room temperature. Even though the compressed product reaches room temperature relatively quickly, it takes the binding system several hours to return to its original form. This is due to the polymorphism of the emulsifier/fat system. During this time, the weak binding system (due to the relatively poor binding characteristics of the components) is converted to a bonding system between the particles in the compressed product. Whereas the fats and emulsifiers are weak binders when the compressed rapid-melt product is first granulated and compressed, the fats and emulsifiers now become a much stronger bonding system.

Optionally, the heating step of the inventive process may be done under vacuum, thus enhancing the bonding of the particles by the fat/emulsifier system.

The rapid-melt compositions of the present inventive subject matter produced by the above methods have increased product integrity and stability. The compositions are "storage stable", meaning that the compositions are stable in the absence of special handling procedures. The inventive compositions are stable both prior to packaging and after packaging. Importantly, the inventive compositions maintain their stability and integrity without refrigeration and without humidity controls being implemented during handling, packaging and storing of the products. Additionally, since the compositions exhibit increased integrity and stability, the compositions can be used in most of the current economical packages suitable for a global environment. Further, high temperatures are not needed when processing the inventive compositions. The only heat that needs to be used during processing is to melt the binder prior to mixing with the other elements.

The following examples are illustrative of preferred embodiments of the invention and are not to be construed as limiting the invention thereto. All percentages are given in weight percent, unless otherwise noted and are based on 100% by weight of the final compositions.

EXAMPLES

Example 1

Preparation of Compressed Rapid-Melt Product Containing Chondroitin and Glucosamine 4.51% cocoa butter, 9.01% sorbitan monostearate, 0.45% lecithin, 0.36% polysorbate 20, 0.45% sodium lauryl sulfate, 0.02% color agent, 0.02% sucralose, 1.62% citric acid and 7.03% chondroitin sulfate were mixed in a heating vessel. The mixture was stirred and heated to a temperature of 130° F. The mixture was maintained at the 130° F. temperature while 34.05% of xylitol powder was added under continual stirring, along with 2.53% powdered flavors pre-blended with 9.01% xylitol powder.

Upon complete blending of the above components, the mixture was transferred to wax paper and cooled to 41° F. for 30 minutes. Once completely cooled, the mixture was milled using a colloidal mill with a #16 screen.

In the meantime, 24.61% encapsulated glucosamine, 4.51% maltodextrin, 0.45% silicon dioxide, 0.90% magnesium stearate, 0.45% additional powdered flavors, and 0.02% color agent were mixed, then passed through a #30 mesh.

After sieving the above mixtures, the two mixtures were blended together and compressed in a conventional compression tableting machine.

In this example, one active ingredient (chondroitin) was added in the emulsifier melting step, while another active (glucosamine) was added during the lubrication step.

Example 2

Preparation of Compressed Rapid-Melt Product Containing Glucosamine 9.5% acetylated monoglycerides, 17.7% hydrogenated vegetable oil and 3.0% monoglycerides were mixed in a suitable vessel and heated to 150° F. to melt the fats. Meanwhile, 68.7% glucosamine hydrochloride powder was pre-blended with 0.8% aspertame and 0.3% sodium laurel sulfate. Once the fats had completely melted, the pre-blended glucosamine hydrochloride mixture was added to the vessel. The fats/glucosamine mixture was them mixed well at 150° F.

Upon complete blending of the above components, the mixture was transferred to wax paper and cooled to 41° F. for 30 minutes. Once completely cooled, the mixture was milled using a colloidal mill with a #16 screen. The resultant product was then compressed in a conventional compression tableting machine.

Example 3

Preparation of Compressed Rapid-Melt Product Containing Calcium 18.80% hydrogenated vegetable oil, 9.68% monoglycerides, 0.48% polysorbate 80, 0.06% sodium lauryl sulfate and 0.02% color agent were mixed and heated in a suitable vessel. The mixture was heated to 130° F. for 10 minutes until the components melted into a solution. 48.76% dextrose powder was added to the mixture under constant stirring along with a pre-blended mixture of 0.04% cooling agent and 1.55% flavors in 12.1% dextrose powder.

Upon complete blending of the above components, the mixture was transferred to wax paper and cooled to 41° F. for 30 minutes. Once completely cooled, the mixture was milled using a colloidal mill with a #16 screen.

In the meantime, 0.28% aspertame, 1.22% powdered flavors, 1.47% silicon dioxide, 1.22% magnesium stearate, 0.6% polyethylene glycol, 3.7% maltodextrin and 0.02% color agents were mixed and passed through a #30 mesh.

After sieving the above mixtures, the two mixtures were blended together and compressed in a conventional compression tableting machine.

Example 4

Preparation of Cellulose-Containing Compressed Rapid-Melt Product with a Bonding Agent A 5.0% hydrocolloidal gum solution in water was prepared. The solution was mixed well and set aside until free from lumps. In the meantime, 73.40% mannitol powder was blended with 24.6% microcrystalline cellulose and 0.21% color agents. After mixing an appropriate time, the gum solution was added to the mixture in small amounts. Just enough gum solution was added to form small lumps or aggregates. The wet aggregates were passed through a #8 screen.

After sieving, the granules were placed on trays and allowed to dry using air heated to greater than 150° F. Once completely dry, the granules were ground to a #40 mesh size. The granules were then loaded into a conventional tableting machine and tablets were produced.

The resultant tablets were of sufficient hardness and provided proper liquification in the mouth.

Example 5

Preparation of Bonded Rapid-Melt Product

Mannitol granules were prepared by mixing 89.00% mannitol with 10.00% microcrystalline cellulose. The mannitol and microcrystalline cellulose were granulated with 1.00% polyvinyl pyrrolidone.

Following granulation of the mannitol, 77.98% of the above mannitol granules were mixed with 0.20% sucrose, 0.05% sodium lauryl sulphate and 0.07% carboxamide. 1.85% suitable flavors and 6.98% encapsulated active ingredients were added to the mixture. Following proper mixing of the mannitol granules with the remaining above ingredients, 10.20% bonding agent, in this case 10.00% sorbitan monostearate and 0.20% Tween 80, along with 1.00% crosspovidone, 0.50% talc, and 0.75% magnesium stearate were added to the mixture. The final mixture was then tableted using 0.75-inch punches.

The resulting product exhibited good granular flow as well as good hardness of the final product. The product was able to be handled and packaged in a conventional manner. The product melted within 25 seconds of being placed in the mouth of a mammal.

Example 6

Preparation of Bonded Rapid-Melt Product

Mannitol granules were prepared by mixing 89.00% mannitol with 10.00% microcrystalline cellulose. The mannitol and microcrystalline cellulose were granulated with 1.00% polyvinyl pyrrolidone.

Following granulation of the mannitol, 79.85% of the above mannitol granules were mixed with 0.20% sucrose, 0.05% sodium lauryl sulphate and 0.07% carboxamide. 1.85% suitable flavors and 6.98% encapsulated active ingredients were added to the mixture. Following proper mixing of the mannitol granules with the remaining above ingredients, 5.00% bonding agent, in this case sorbitan monostearate, and 5.00% talc as a lubricant, along with 1.00% crosspovidone were added to the mixture. The final mixture was then tableted using 0.75-inch punches.

The resulting product exhibited good granular flow as well as good hardness of the final product. The product was able to be handled and packaged in a conventional manner. The product melted within 10 seconds of being placed in the mouth of a mammal.

Example 7

Preparation of a Non-Bonded Rapid-Melt Product

Mannitol granules were prepared by mixing 89.00% mannitol with 10.00% microcrystalline cellulose. The mannitol and microcrystalline cellulose were granulated with 1.00% polyvinyl pyrrolidone.

Following granulation of the mannitol, 89.95% of the above mannitol granules were mixed with 0.20% sucrose, 0.05% sodium lauryl sulphate and 0.07% carboxamide. 1.85% suitable flavors and 6.98% encapsulated active ingredients were added to the mixture. Following proper mixing of the mannitol granules with the remaining above ingredients 1.00% crosspovidone was added to the mixture. The final mixture was then tableted using 0.75-inch punches.

The resulting product exhibited good granular flow; however, the product was very brittle and easily crumbled when pressed between one's fingers. The product would not have been easily handled or packaged.

The inventive subject matter being thus described, it will be obvious that the same may be varied in many ways. Such variations are not to be regarded as a departure from the spirit and scope of the inventive subject matter, and all such modifications are intended to be included within the scope of the following claims.

What is claimed is:

1. A method of preparing an oral dosage composition that rapidly disintegrates in a mouth of a mammal comprising the steps of:
   a) melting at least one binder in an amount from about 0.01% to about 70% by weight with a salivating agent in an amount from about 0.05% to about 15% by weight, to form a first mixture
      wherein said binder is selected from the group consisting of cocoa butter, hydrogenated tallow, hydrogenated vegetable oils, hydrogenated cotton seed oil, palm kernel oil, soybean oil, stannol esters, polyethylene glycols, polysaccharides, gum solutions, corn syrup, hydrogenated starch hydrolates, glycerine, polypropylene glycol, and mixtures thereof, and
      wherein said salivating agent is selected from the group consisting of alkyl aryl sulfonates, alkyl sulfates, sulfonated amides and amines, sulfated and sulfonated esters and ethers, alkyl sulfonates, polyethoxlyated esters, mono- and diglycerides, diacetyl tartaric esters of monoglycerides, polyglycerol esters, sorbitan esters and ethoxylates, lactylated esters, phospholipids such as lecithin, polyoxyethylene sorbitan esters, proplyene glycol esters, sucrose esters, and mixtures thereof;
   b) mixing a therapeutically effective amount of an active ingredient with at least one lubricant to form a second mixture wherein said lubricant is selected from the group consisting of fats, emulsifiers, magnesium stearate, calcium stearate, talc, starches, silicon dioxide, and mixtures thereof;
   c) combining said first mixture with said second mixture to form a compressible mixture;
   d) compressing said compressible mixture into an oral dosage composition;
   e) heating said oral dosage composition to a temperature 40 to 60° C. for a period of 1 to 10 minutes in order to convert said kinder to a bonding agent; and
   f) cooling said heated oral dosage composition,
   wherein said composition disintegrates without the necessity of biting or chewing in the mouth of said mammal less than 20 seconds of administration.

2. The method according to claim 1 wherein said heating step is carried out by heating said oral dosage composition to a temperature of 45 to 55° C.

3. The method according to claim 1 wherein said heating step is carried out for 2 to 5 minutes.

4. The method according to claim 1 wherein said heating step is carried out by heating said oral dosage composition to a temperature of 45 to 55° C. for 2 to 5 minutes.

5. The method according to claim 1 further comprising the step of granulating said first mixture prior to combining with said second mixture.

6. The method according to claim 5 wherein said second mixture is granulated.

7. The method according to claim 1 wherein said active ingredient is selected from the group consisting of psychorropics, gastrointestinal therapeutics, cardiovascular therapeutics, migraine therapeutics, inflammation therapeutics, benign prostatic hypertrophy therapeutics, fungal therapeutics, allergic rhinitis therapeutics, anticonvulsants, and viral therapeutics.

* * * * *